(12) United States Patent
Walsh et al.

(10) Patent No.: US 10,190,057 B2
(45) Date of Patent: Jan. 29, 2019

(54) FISCHER-TROPSCH SYNTHESIS

(71) Applicant: Sasol Technology Proprietary Limited, Sandton (ZA)

(72) Inventors: Richard Neil Walsh, Parys (ZA); Jean Louis Gauché, Parys (ZA); Hendrik Wilhelmus Joubert, Doha (QA); Albertus Maritz Van Wyk, Doha (QA); Johannes Henning Viljoen, Doha (QA); Marcel Juergen Krause, Doha (QA)

(73) Assignee: SASOL TECHNOLOGY PROPRIETARY LIMITED, Sandton (ZA)

( * ) Notice: Subject to any disclaimer, the term of this patent is extended or adjusted under 35 U.S.C. 154(b) by 0 days.

(21) Appl. No.: 15/524,859

(22) PCT Filed: Oct. 26, 2015

(86) PCT No.: PCT/ZA2015/050016
§ 371 (c)(1),
(2) Date: May 5, 2017

(87) PCT Pub. No.: WO2016/081956
PCT Pub. Date: May 26, 2016

(65) Prior Publication Data
US 2017/0321126 A1    Nov. 9, 2017

(30) Foreign Application Priority Data
Nov. 20, 2014    (ZA) .................................. 2014/08551

(51) Int. Cl.
*C10G 2/00*    (2006.01)
*C10G 3/00*    (2006.01)
(Continued)

(52) U.S. Cl.
CPC .............. *C10G 2/343* (2013.01); *B01J 23/94* (2013.01); *B01J 38/10* (2013.01); *B01J 38/12* (2013.01);
(Continued)

(58) Field of Classification Search
CPC . C10G 2/232; C10G 2/30; C10G 2/32; C10G 3/62; B01J 38/10; B01J 38/12; B01J 23/75; C07C 10/45
See application file for complete search history.

(56) References Cited

U.S. PATENT DOCUMENTS 6,458,857 B1    10/2002    Wittenbrink et al.
9,090,832 B2    7/2015    Heraud et al.
(Continued)

FOREIGN PATENT DOCUMENTS

WO    2009/035974 A1    3/2009

OTHER PUBLICATIONS

International Preliminary Report on Patentability, dated Jan. 20, 2017, for International Application No. PCT/ZA2015/050016, 6 pages.
(Continued)

*Primary Examiner* — Jafar F Parsa
(74) *Attorney, Agent, or Firm* — Seed IP Law Group LLP

(57) ABSTRACT

A method (10) of synthesizing Fischer-Tropsch products (20) includes feeding a synthesis gas (30) to a moving-bed Fischer-Tropsch synthesis reactor (16) containing a Fischer-Tropsch catalyst in a moving catalyst bed and catalytically converting at least a portion of the synthesis gas (30) in the moving catalyst bed to Fischer-Tropsch products (20). The Fischer-Tropsch products (20) are removed from the moving-bed Fischer-Tropsch synthesis reactor (16). The method (10) further includes, while the moving-bed Fisher-Tropsch synthesis reactor (16) is on-line, withdrawing a portion (50)
(Continued)

of the Fischer-Tropsch catalyst from the moving-bed Fischer-Tropsch synthesis reactor (16), adding a reactivated Fischer-Tropsch catalyst (57, 58) to the moving-bed Fischer-Tropsch synthesis reactor (16), and adding a fresh Fischer-Tropsch catalyst (60,58), in addition to the reactivated catalyst (57,58), to the moving-bed Fischer-Tropsch synthesis reactor (16).

9 Claims, 3 Drawing Sheets

(51) Int. Cl.
*C07C 1/04* (2006.01)
*B01J 38/10* (2006.01)
*B01J 23/94* (2006.01)
*B01J 38/72* (2006.01)
*B01J 38/18* (2006.01)
*B01J 38/12* (2006.01)

(52) U.S. Cl.
CPC ............ *B01J 38/18* (2013.01); *B01J 38/72* (2013.01); *C07C 1/045* (2013.01); *C10G 2/33* (2013.01); *C10G 2/342* (2013.01); *C10G 3/62* (2013.01); *C07C 2523/75* (2013.01); *Y02P 30/20* (2015.11)

(56) References Cited

U.S. PATENT DOCUMENTS

2004/0259963 A1 12/2004 Huang et al.
2013/0210939 A1 8/2013 Rytter et al.

OTHER PUBLICATIONS

International Search Report, dated Apr. 25, 2016, for International Application No. PCT/ZA2015/050016, 2 pages.
Written Opinion of the International Searching Authority, dated May 26, 2016, for International Application No. PCT/ZA2015/050016, 5 pages.

FISCHER-TROPSCH SYNTHESIS

FIELD OF THE INVENTION

This invention relates to Fischer-Tropsch synthesis. In particular, the invention relates to a method of synthesising Fischer-Tropsch products.

BACKGROUND OF THE INVENTION

In Fischer-Tropsch synthesis, synthesis gas comprising carbon monoxide and hydrogen is converted to mostly hydrocarbons and water over a heterogeneous catalyst. Although various metals are known to catalyse Fischer-Tropsch synthesis reactions, only catalysts comprising iron (Fe) or cobalt (Co) have found large scale commercial application to date.

Fischer-Tropsch synthesis can be applied in a variety of reactors, as discussed, for example, in the book entitled "Fischer-Tropsch Technology", Dry and Steynberg (Eds.), *Stud. Surf. Sci. Catal.*, Vol. 152, October 2004 (Elsevier). The reactors can broadly be divided into two groups, namely stationary bed reactors and moving bed reactors. In stationary bed reactors, the catalyst bed is typically fixed in one position. Examples of stationary bed reactors include multi-tubular fixed bed reactors and micro-channel reactors. In moving bed reactors, catalyst particles move around freely inside the reactor. Examples of moving bed reactors include two-phase fluidised bed and three-phase slurry bed reactors.

Fischer-Tropsch catalysts deactivate under synthesis conditions (i.e. conditions of elevated temperatures and pressures) for a variety of reasons, including, for example, by poisoning due to nitrogen- or sulphur-containing compounds present in the synthesis gas, sintering of metal crystallites in the catalyst itself and coke deposition on active catalyst sites. Water is a by-product of the Fischer-Tropsch reaction and is well known to contribute to the deactivation of the catalyst. The rate of deactivation of the catalyst is a function of both the catalyst itself, for example catalyst composition, method of preparation, etc., and the process conditions under which it is operated and to which it is exposed, for example the level or concentration of poisons in synthesis feed gas, reactor operating temperature, reagent partial pressures, conversion, etc.

Certain catalyst deactivation mechanisms are readily reversible, for example by subjecting the catalyst to a treatment involving contacting the catalyst with a reducing gas such as a hydrogen containing gas. Other deactivation mechanisms may only be reversed by more severe treatments, for example by treatment processes comprising multiple steps which would typically involve steps of reducing a wax content of the catalyst (for example by settling out the catalyst from a catalyst slurry (i.e. a catalyst-containing slurry), followed by a solvent wash or a hydrogen treatment), exposure of the catalyst to an oxygen containing gas inter alia to burn off or oxidise carbonaceous deposits on the catalyst, and finally a reduction step in which the catalyst is activated for use in the Fischer-Tropsch synthesis, for example by reduction with a hydrogen containing gas.

Since a hydrogen rejuvenation treatment is only able to reverse a limited number of the catalyst deactivation mechanisms, it is normally less efficient in restoring catalyst activity than an oxidative regeneration treatment, especially for older catalysts. Over time, due to an accumulation of deactivation effects that are not reversible by a rejuvenation treatment, the catalyst will become less and less active and ultimately unfit for further use if only reactivation by way of rejuvenation treatment is applied. On the other hand, a regeneration (oxidative) treatment is usually more aggressive than a rejuvenation treatment (e.g. by hydrogen reduction), since it exposes the catalyst to much higher temperatures, often in the presence of steam formed in the oxidation step.

Amongst others, the hydrothermal conditions to which a catalyst is exposed in a regeneration treatment could lead to a deterioration of the catalyst over time, often limiting the number of regeneration treatments to which a catalyst can be sensibly exposed. For example, as a catalyst is exposed to an increasing number of reactivation treatments, reactivation becomes increasingly less effective in restoring catalyst performance. This is mainly due to the cumulative negative effects of multiple reactivation treatments on catalyst integrity and activity. For instance, Shell has reported that the overall catalyst lifetime of their commercial fixed bed Fischer-Tropsch catalyst can be extended to five years by performing an annual regeneration treatment (A. Hoek, L. B. J. M. Kersten, "The Shell Middle Distillate Synthesis Process: technology, products and perspective", *Stud. Surf. Sci Catal.*, Vol. 147 (Nat. Gas. Cony. VII), pp. 25-28). This implies that the Shell fixed-bed Fischer-Tropsch catalyst can be subjected to four regeneration cycles before it becomes unfit for further use, after which the fixed-bed Fischer-Tropsch reactor must be reloaded with a fresh batch of catalyst in order that a new production cycle can be initiated.

When a Fischer-Tropsch synthesis process is operated in a fixed bed reactor, it is not always convenient to remove the catalyst from the reactor for purposes of reactivation. The reactivation process to recover some or all of the lost activity of the catalyst is then often rather effected in situ. A disadvantage of in situ reactivation is that the operation of the Fischer-Tropsch synthesis process has to be suspended or interrupted before the reactivation can be performed, i.e. the reactivation is performed off-line. Depending on the reactivation process, this can result in a lengthy interruption of Fisher-Tropsch synthesis. For example, delays may be caused by heating up or cooling down the catalyst bed during or between steps of the reactivation process or purging of the Fischer-Tropsch reactor to avoid the possibility of forming explosive gas mixtures in case where an oxidative step is applied in the reactivation process. Typically, the full catalyst inventory is reactivated during an off-line in situ reactivation process, meaning that all catalyst particles in the Fischer-Tropsch reactor would be subjected to an equal number of reactivation treatments.

Moving bed reactors have the advantage that catalyst can usually be withdrawn or added during normal operation without significantly affecting the Fischer-Tropsch synthesis reactions. This affords an operator the opportunity of withdrawing a portion of the catalyst inventory from a Fisher-Tropsch reactor, subjecting it to a reactivation treatment in order to restore some or all of the catalyst activity and returning the reactivated catalyst to the Fischer-Tropsch reactor for further use, while keeping the Fischer-Tropsch reactor on-line. Various methods for the on-line withdrawal and reactivation of Fischer-Tropsch catalyst have been suggested in the prior art.

In U.S. Pat. No. 5,260,239 a reactor arrangement that allows for the continuous circulation of catalyst slurry between a slurry phase Fischer-Tropsch reactor and a slurry phase hydrogen rejuvenation reactor by using a system of downcomers is disclosed. Catalyst slurry containing partially deactivated catalyst is fed under flow of gravity from the Fischer-Tropsch reactor to the rejuvenation vessel where it is exposed to hydrogen in order to recover some of the lost activity, while slurry containing rejuvenated catalyst is cycled back to the Fischer-Tropsch reactor.

U.S. Pat. No. 6,900,151 discloses a slurry phase Fischer-Tropsch process which involves the regeneration of catalyst. Slurry containing catalyst is withdrawn from the Fischer-Tropsch reactor and regenerated via an oxidative treatment, leaving the active metals in the oxide phase. The slurry Fischer-Tropsch reactor, which is supplied with an in situ hydrogen rejuvenation means, receives the catalyst in unreduced (oxidised) form, whereafter it is reduced in situ to the metallic state by contact with hydrogen.

In U.S. Pat. No. 6,900,151, the treatment of a deactivated catalyst only with a reducing gas in order to increase its activity is typically called rejuvenation, whereas a treatment involving at least an oxidative step is called regeneration. It will be apparent from an assessment of the art that in other instances regeneration may refer to any treatment of a deactivated catalyst in order to recover some or all of its activity. A clear definition of the relevant technical terms is essential for a proper understanding of the present invention.

In this specification, hereinafter: (i) the term "reactivation" should be understood to mean any method of treating a partially deactivated catalyst in order to recover at least some of its lost activity and thus includes "regeneration" and "rejuvenation", so that a reactivated catalyst can be a regenerated catalyst, or a rejuvenated catalyst, or a catalyst that has been both regenerated and rejuvenated; (ii) the term "rejuvenation" should be understood to mean a treatment of a deactivated catalyst by contact with a reducing agent, for example by contact with a hydrogen containing gas, but without contact with an oxidising agent, in order to recover at least some of its lost activity; and (iii) the term "regeneration" should be understood to mean a treatment of a deactivated catalyst by contact with an oxidising agent, for example an oxygen containing gas, in at least one step of a reactivation treatment in order to recover at least some of its lost activity.

Furthermore, the term "fresh catalyst" should be understood to mean a newly manufactured or never before used catalyst, i.e. a catalyst that has never before been used to produce Fischer-Tropsch products under synthesis conditions, whereas the term "reactivated catalyst" should be understood to mean a used catalyst that has been subjected to reactivation.

WO 2001/036352 discloses a Fischer-Tropsch process in which catalyst is regenerated by means of a steam treatment. WO 2001/036352 also teaches cycling of catalyst between the Fischer-Tropsch synthesis process and a regeneration process on a continuous basis.

U.S. Pat. No. 6,201,030 describes a slurry Fischer-Tropsch reactor with two regenerators. In the process of U.S. Pat. No. 6,201,030 a deactivated catalyst is unloaded to one regenerator whilst regenerated catalyst is returned to the slurry Fischer-Tropsch reactor from another regenerator.

US 2005/0124706 discloses a process of cycling catalyst batches between a slurry phase Fischer-Tropsch reactor and a regeneration process by applying a pressure swing condition to a catalyst.

US 2010/0240777 discloses a slurry phase Fischer-Tropsch process in which the activity of a deactivated catalyst is restored by subjecting the catalyst to a hydrogen treatment. The exposure of the catalyst to hydrogen is effected either inside the synthesis reactor or in an external circulation stream of catalyst slurry. US 2010/0240777 terms contact with hydrogen a "regeneration" of the catalyst, but since this only entails exposing the catalyst to a reducing gas, it is rather a rejuvenation in terms of the defined terminology in the present specification.

WO 2003/064356 and WO 2003/064034 both describe the removal of slurry containing deactivated catalyst from a slurry reactor, subjecting it to a regeneration treatment and returning the catalyst to the reactor. Provision is made for the removal of fine particles from the withdrawn slurry. Preferably, the removal of fine particles is done as part of the regeneration process. Catalyst fines are undesirable for slurry reactor operations as they can lead to operational problems. Both WO 2003/064356 and WO 2003/064034 thus teach that the regeneration procedure can advantageously also be used for the reduction of undesirable fines inside the slurry phase Fischer-Tropsch reactor.

WO 2012/022942 also describes a slurry Fischer-Tropsch process in which batches of slurry containing deactivated catalyst are removed from a Fischer-Tropsch synthesis reactor and subjected to a regeneration treatment. Preferably, undesirable catalyst fines are removed from the regenerated catalyst before it is reloaded back into the Fischer-Tropsch synthesis reactor in order to mitigate the adverse effects of fine particles on slurry reactor operation.

WO 2012/056346 discloses a method of operating a process for catalytically converting one or more reactants to one or more products using a fluid bed reactor (e.g. a three-phase slurry bed reactor) containing a catalyst (e.g. a Fischer-Tropsch catalyst) which deactivates over time. The method includes adding a catalyst which has the tendency to increase the conversion rate of one or more reactants into the reactor, and reducing the operating temperature of the reactor to counteract to at least some extent the effect of the added catalyst on the conversion rate of the one or more reactants.

Methods of removing catalyst from a Fischer-Tropsch synthesis reactor, subjecting the removed catalyst to a treatment in order to regain some or all of its activity and returning the reactivated catalyst to the Fischer-Tropsch synthesis reactor are therefore known in the prior art. Additionally, the art teaches that the reactivation step can conveniently also be used to remove undesirable catalyst fines, generated either during the Fischer-Tropsch synthesis process or during the reactivation process itself, from a slurry reactor.

In a moving-bed reactor, such as a three-phase slurry bubble column Fischer-Tropsch synthesis reactor, the catalyst particles can move around freely and are essentially well mixed. It follows that the catalyst particles withdrawn from such a Fischer-Tropsch synthesis reactor for reactivation is a random sample of catalyst particles present therein. Therefore, in a Fischer-Tropsch reactor in which on-line reactivation of catalyst is employed, a distribution of catalyst particles with different activities will be present depending on the reactivation history of each catalyst particle. Furthermore, a distribution of catalyst particles that has been exposed to varying numbers of reactivation treatments will develop over time, i.e. some catalyst particles might have undergone a large number of reactivation treatments, whereas other catalyst particles might not have been reactivated at all. This is particularly important where the reactivation treatment includes regeneration. Additionally, Fischer-Tropsch synthesis reactor performance will increasingly deteriorate as a portion of the catalyst inventory inside the Fischer-Tropsch reactor that is no longer suitably reactivated by the reactivation treatment continuously increases over time. Eventually this drop in Fischer-Tropsch synthesis reactor performance will necessitate a discarding of the whole catalyst inventory and restarting with fresh catalyst. This in turn requires interruption of plant operation and is therefore undesirable. The prior art has failed to address these issues.

A method of synthesising Fisher-Tropsch products which employs catalyst reactivation and which allows for extended, stable on-line operation would be an advantage.

BRIEF DESCRIPTION OF THE INVENTION

According to the invention there is provided a method of synthesising Fischer-Tropsch products, the method including feeding a synthesis gas to a moving-bed Fischer-Tropsch synthesis reactor containing a Fischer-Tropsch catalyst in a moving catalyst bed, catalytically converting at least a portion of the synthesis gas in the moving catalyst bed to Fischer-Tropsch products and withdrawing the Fischer-Tropsch products from the moving-bed Fischer-Tropsch synthesis reactor, the method further including, while the moving-bed Fisher-Tropsch synthesis reactor is on-line:

withdrawing a portion of the Fischer-Tropsch catalyst from the moving-bed Fischer-Tropsch synthesis reactor;

adding a reactivated Fischer-Tropsch catalyst to the moving-bed Fischer-Tropsch synthesis reactor; and adding a fresh Fischer-Tropsch catalyst, in addition to the reactivated catalyst, to the moving-bed Fischer-Tropsch synthesis reactor.

By "on-line" is meant that the withdrawal or addition of Fischer-Tropsch catalyst from the moving-bed Fischer-Tropsch synthesis reactor does not interrupt the conversion of synthesis gas into Fischer-Tropsch products.

The addition of catalyst to the moving-bed Fischer-Tropsch synthesis reactor may be done according to the teachings of WO 2012/056346.

The moving-bed Fischer-Tropsch synthesis reactor may be a slurry phase reactor. In other words, the moving catalyst bed may be a three-phase slurry bed of catalyst particles suspended in a suspension medium. In particular, the moving-bed Fischer-Tropsch synthesis reactor may be a three-phase slurry bubble column reactor, e.g. a Sasol Slurry Phase Distillate (trade name) reactor. In an alternative embodiment, the moving-bed Fischer-Tropsch synthesis reactor may be a two phase fluidised bed reactor, e.g. a Sasol Advanced Synthol (trade name) reactor. In other words, the moving catalyst bed may be a two-phase fluidised bed of catalyst particles fluidised by a fluidisation medium, e.g. synthesis gas.

The Fisher-Tropsch catalyst may be an iron catalyst or a cobalt catalyst. Preferably, the Fischer-Tropsch catalyst is a cobalt catalyst. In a preferred embodiment of the invention, the Fischer-Tropsch catalyst is a supported cobalt catalyst, more preferably an alumina-supported cobalt catalyst.

The iron catalyst may be a precipitated iron catalyst.

The moving-bed Fischer-Tropsch synthesis reactor may be operated at an operating temperature in the range of from about 200° C. to about 370° C.

Where the moving-bed Fischer-Tropsch synthesis reactor is a slurry phase reactor which employs a supported cobalt catalyst, the operating temperature of the moving-bed Fischer-Tropsch synthesis reactor may be in the range of from about 200° C. to about 240° C.

Where the moving-bed Fischer-Tropsch synthesis reactor is a slurry phase reactor which employs an iron catalyst, the operating temperature of the moving-bed Fischer-Tropsch synthesis reactor may be in the range of from about 220° C. to about 280° C.

Where the moving-bed Fischer-Tropsch synthesis reactor is a two phase fluidised bed reactor which employs an iron catalyst, the operating temperature of the moving-bed Fischer-Tropsch synthesis reactor may be in the range of from about 300° C. to about 370° C., preferably in the range of from about 330° C. to about 350° C.

The Fischer-Tropsch products may be hydrocarbon products in the range of normally gaseous hydrocarbons to liquid and waxy hydrocarbons. The Fischer-Tropsch products may include water. Furthermore, the Fischer-Tropsch products may include oxygenates. Typically, the Fisher-Tropsch products are a combination of hydrocarbon products, water and oxygenates.

The withdrawn Fischer-Tropsch catalyst may be in the form of a catalyst slurry. The catalyst slurry may include catalyst particles and Fisher-Tropsch products.

At least a portion of the withdrawn Fischer-Tropsch catalyst may be subjected to a reactivation treatment thereby to produce at least a portion of the reactivated Fischer-Tropsch catalyst. Typically, the reactivated Fischer-Tropsch catalyst is returned to the moving-bed Fischer-Tropsch synthesis reactor from which it was withdrawn. However, it may also be possible to employ the reactivated Fischer-Tropsch catalyst in a moving-bed Fischer-Tropsch synthesis reactor different form the one from which it was withdrawn, e.g. by having a catalyst reactivation unit that serves a number of Fischer-Tropsch synthesis reactors.

The reactivation treatment may include a regeneration treatment. The regeneration treatment may include, amongst others, a step of exposing the withdrawn catalyst to oxygen.

The regeneration treatment may further include a reduction step. The reduction step may include exposing the withdrawn Fisher-Tropsch catalyst to hydrogen, subsequent to exposing the withdrawn Fischer-Tropsch catalyst to oxygen.

The reactivation treatment may include a rejuvenation treatment. The rejuvenation treatment may include exposing the withdrawn Fischer-Tropsch catalyst to hydrogen.

Where the moving-bed Fischer-Tropsch synthesis reactor is a three-phase slurry bubble column reactor, the moving-bed Fischer-Tropsch synthesis reactor may have a Fischer-Tropsch catalyst concentration in the range of from about 5 vol % to about 50 vol %, preferably in the range from about 20 vol % to about 40 vol % of a total volume of catalyst and slurry liquid in the moving-bed Fischer-Tropsch synthesis reactor.

The on-line withdrawal of a portion of the Fischer-Tropsch catalyst from the moving-bed Fischer-Tropsch synthesis reactor may be done continuously or batch-wise.

Where the on-line withdrawal of the portion of the Fischer-Tropsch catalyst from the moving-bed Fischer-Tropsch synthesis reactor is continuous, the portion of the Fischer-Tropsch catalyst may be withdrawn from the moving-bed Fischer-Tropsch synthesis reactor at a rate of from about 0.1 wt % to about 5 wt %, more preferably from about 0.5 wt % to about 2 wt %, e.g. about 1 wt % of a Fischer-Tropsch catalyst inventory in the moving-bed Fischer-Tropsch reactor per day.

Typically, the Fisher-Tropsch catalyst inventory is the mass of Fisher-Tropsch catalyst in the moving-bed Fisher-Tropsch synthesis reactor.

Where the on-line withdrawal of the portion of the Fischer-Tropsch catalyst from the moving-bed Fischer-Tropsch synthesis reactor is batch-wise, the portion of the Fischer-Tropsch catalyst withdrawn from the moving-bed Fisher-Tropsch synthesis reactor per batch may be in the range of from about 0.1 wt % to about 10 wt %, preferably from about 3 wt % to about 7 wt %, e.g. about 5 wt %, of the Fischer-Tropsch catalyst inventory in the moving-bed Fisher-Tropsch synthesis reactor.

As mentioned hereinbefore, a regeneration treatment is usually more aggressive than a rejuvenation treatment, since it exposes the catalyst to much higher temperatures, often in the presence of steam formed in the oxidation step. Amongst others, the hydrothermal conditions to which a catalyst is exposed in a regeneration treatment could lead to a deterioration of the catalyst over time, often limiting the number of regeneration treatments to which a catalyst can be sensibly exposed.

On the other hand, a rejuvenation treatment is only able to reverse a limited number of catalyst deactivation mechanisms. Over time, due to an accumulation of deactivation effects that are not reversible by a rejuvenation treatment, the catalyst will become less and less active and ultimately unfit for further use if only reactivation by way of rejuvenation is applied.

Thus, in a preferred embodiment of the invention, the method further includes discarding at least a portion of the withdrawn Fischer-Tropsch catalyst.

Discarding a portion of the withdrawn Fischer-Tropsch catalyst provides a purge for Fischer-Tropsch catalyst and, in conjunction with the addition of fresh Fischer-Tropsch catalyst to the moving-bed Fischer-Tropsch synthesis reactor, allows for extended stable operation. Since there is no practical method known to the inventors to segregate a mixture of Fischer-Tropsch catalyst on the basis of its activity or performance, the discarded portion of Fischer-Tropsch catalyst will be substantially representative of the catalyst inventory in the moving-bed Fischer-Tropsch synthesis reactor.

However, segregation of Fischer-Tropsch catalyst on the basis of size is readily achievable. The method may thus further include selectively removing fine catalyst particles from the withdrawn Fischer-Tropsch catalyst.

The discarded portion of withdrawn Fischer-Tropsch catalyst may be subjected to a process in which at least a portion of the metals are reclaimed therefrom.

The discarded portion of Fischer-Tropsch catalyst may be in the range of from about 15 wt % to about 60 wt %, preferably from about 20 wt % to about 55 wt %, more preferably from about 25 wt % to about 50 wt % of the withdrawn Fischer-Tropsch catalyst.

The fresh Fischer-Tropsch catalyst may be added to the moving-bed Fischer-Tropsch synthesis reactor in a mass required to maintain a desired Fischer-Tropsch reactor productivity.

The reactor productivity can be defined in any way that is suitable for the involved process. For example, the Fischer-Tropsch reactor productivity can be expressed as the mass of hydrocarbon produced per unit time, as the rate of CO conversion to hydrocarbons on a mass or molar basis, or the like.

The fresh Fischer-Tropsch catalyst may be added continuously or batch-wise to the moving-bed Fischer-Tropsch synthesis reactor.

Where the fresh Fischer-Tropsch catalyst is added batch-wise to the moving-bed Fisher-Tropsch synthesis reactor, the batches of fresh Fisher-Tropsch catalyst may be from about 0.1 wt % to about 6 wt %, preferably from about 1 wt % to about 3 wt % of the Fischer-Tropsch catalyst inventory in the moving-bed Fischer-Tropsch synthesis reactor.

Where the fresh Fischer-Tropsch catalyst is added continuously to the moving-bed Fischer-Tropsch synthesis reactor, the fresh Fischer-Tropsch catalyst may be added to the moving-bed Fischer-Tropsch synthesis reactor at a rate of from about 0.02 wt % to about 3 wt %, more preferably from about 0.1 wt % to about 1.5 wt %, e.g. about 1 wt % of the Fischer-Tropsch catalyst inventory in the moving-bed Fischer-Tropsch reactor per day.

In one embodiment of the invention, the fresh Fischer-Tropsch catalyst is added to the moving-bed Fischer-Tropsch synthesis reactor in a mass which is selected to match the mass of the discarded portion of withdrawn Fischer-Tropsch catalyst.

The fresh Fischer-Tropsch catalyst added to the moving-bed Fischer-Tropsch synthesis reactor may be selected so that the Fischer-Tropsch catalyst inventory in the moving-bed Fischer-Tropsch synthesis reactor does not exceed a maximum Fisher-Tropsch catalyst inventory.

Where the reactivation treatment includes regeneration, the moving-bed Fischer-Tropsch synthesis reactor may be operated such that a maximum amount of Fisher-Tropsch catalyst in the moving-bed Fischer-Tropsch synthesis reactor that has been exposed to a maximum number of regeneration treatments is less than about 10 wt %, preferably less than about 5 wt %, more preferably less than about 3 wt %, e.g. about 2.5 wt % of the Fischer-Tropsch catalyst inventory of the moving-bed Fischer-Tropsch synthesis reactor.

The maximum number of regeneration treatments is dependent, amongst others, on the catalyst itself, the hydrothermal conditions to which it is exposed in a regeneration treatment and the process or synthesis conditions under which it is operated during operation. Typically, the maximum number of regeneration cycles is about ten cycles, more typically about six cycles. In certain instances the maximum number of regeneration cycles may even be about four cycles.

The maximum amount of Fisher-Tropsch catalyst in the moving-bed Fischer-Tropsch synthesis reactor that has been subjected to the maximum number of regeneration treatments may be controlled by manipulating relative proportions between the withdrawn Fischer-Tropsch catalyst, the discarded Fischer-Tropsch catalyst, the regenerated Fischer-Tropsch catalyst added to the moving-bed Fischer-Tropsch synthesis reactor and the fresh Fischer-Tropsch catalyst added to the moving-bed Fischer-Tropsch synthesis reactor.

The moving-bed Fisher-Tropsch synthesis reactor may be operated such that an average activity of the Fischer-Tropsch catalyst in the moving-bed Fischer-Tropsch synthesis reactor is in the range of from about 25% to about 75%, preferably from about 30% to about 60%, e.g. at least about 50%, of a starting activity of fresh Fischer-Tropsch catalyst.

The reactivated Fischer-Tropsch catalyst may be added to the moving-bed Fischer-Tropsch synthesis reactor separately from or mixed with the fresh Fischer-Tropsch synthesis catalyst. Preferably, the reactivated Fischer-Tropsch catalyst is mixed with the fresh Fischer-Tropsch catalyst prior to being added to the moving-bed Fischer-Tropsch synthesis reactor.

DETAILED DESCRIPTION OF THE INVENTION

The invention will now be described, by way of example, with reference to the accompanying diagrammatic drawings in which.

Figure 1:
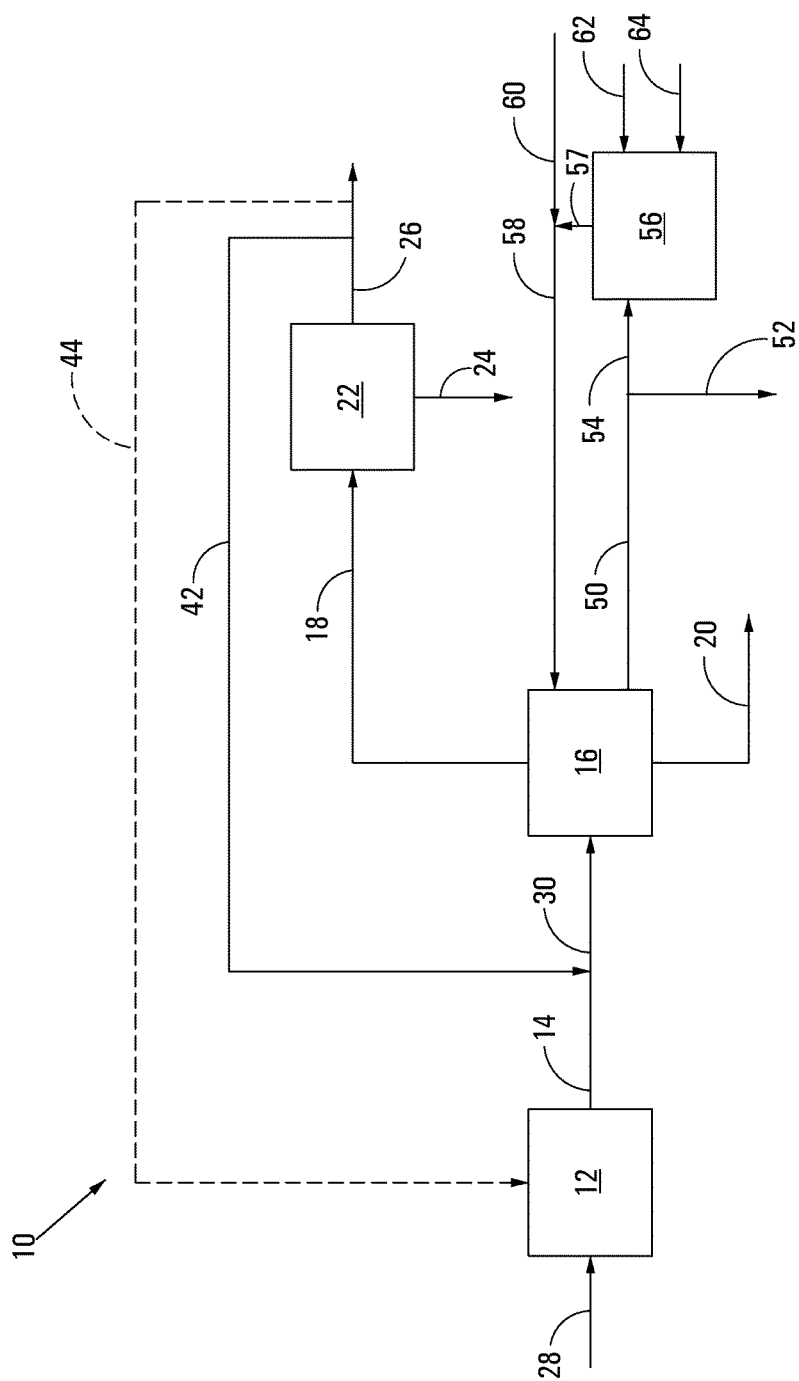
FIG. 1 is a diagrammatic representation of a process employing a method of synthesising Fischer-Tropsch products in accordance with the invention.

With reference to FIG. 1 of the drawings, reference numeral 10 generally indicates a process employing an embodiment of the method of the invention. The process 10 includes broadly a synthesis gas generation stage 12, a moving-bed Fischer-Tropsch synthesis reactor 16, a cooling stage 22 and a catalyst reactivation facility 56.

Carbonaceous or hydrocarbonaceous feed material 28 is fed to the synthesis gas generation stage 12 which is operated to produce fresh synthesis gas 14 which includes $H_2$ and CO. The fresh synthesis gas 14 is fed to the moving-bed Fischer-Tropsch synthesis reactor 16 in which the $H_2$ and CO are catalytically converted in the presence of a Fischer-Tropsch catalyst into Fischer Tropsch products. The Fischer-Tropsch products range from normally gaseous hydrocarbons to liquid and waxy hydrocarbons, as well as water and oxygenates. The gaseous hydrocarbons include methane and $C_2$ hydrocarbons, unreacted synthesis gas components such as $H_2$ and CO, as well as $CO_2$.

The synthesis gas generation stage 12 may be any synthesis gas generation stage, e.g. a coal gasification stage or a natural gas reforming stage, producing a synthesis gas which is suitable for Fischer-Tropsch synthesis. The synthesis gas from the synthesis gas generation stage 12 may be subjected to one or more gas cleaning steps (not shown), where known Fischer-Tropsch catalyst poisons (e.g. $H_2S$, COS, $NH_3$, etc.) or other components (e.g. $CO_2$) are removed from the synthesis gas upstream of the moving-bed Fischer-Tropsch synthesis reactor 16. The operation of such a synthesis gas generation stage 12 and the optional gas clean-up steps are well known to those skilled in the art and are thus not described in any detail. Similarly, the operation of such a moving-bed Fischer-Tropsch synthesis reactor 16 is well known to those skilled in the art and is thus not described in any detail.

The Fischer-Tropsch liquid and waxy products are withdrawn as a liquid product stream 20 from the moving-bed Fischer-Tropsch synthesis reactor 16. The gaseous products are withdrawn from the moving-bed Fischer-Tropsch synthesis reactor 16 as a gaseous product stream 18. The gaseous product stream 18 from the moving-bed Fischer-Tropsch synthesis reactor 16 is cooled in the cooling stage 22 to condense water and other condensable components such as oxygenates therefrom, with the condensed components being separated and withdrawn as a stream 24. Cooled tail gas 26 containing methane and $C_2$ hydrocarbons, unreacted synthesis gas components such as $H_2$ and CO, as well as $CO_2$ is withdrawn from the cooling stage 22.

A portion of the tail gas 26 produced by the moving-bed Fischer-Tropsch synthesis reactor 16 and withdrawn from the cooling stage 22 is optionally recycled back to the moving-bed Fischer-Tropsch synthesis reactor 16, as recycle tail gas as indicated by a dotted flow line 42. A feed synthesis gas 30 entering the moving-bed Fischer-Tropsch synthesis reactor 16 is thus an admixture of recycled tail gas 42 and fresh synthesis gas 14. Optionally, a portion of the Fischer-Tropsch tail gas 26 may be recycled to the synthesis gas generation stage 12, as shown by a dotted flow line 44.

In accordance with the method of the invention, a portion of Fischer-Tropsch catalyst is withdrawn from the moving-bed Fischer-Tropsch synthesis reactor 16 via flow a line 50. The Fisher-Tropsch catalyst so withdrawn is in the form of a slurry of Fisher-Tropsch catalyst (i.e. Fisher-Tropsch catalyst particles), Fischer-Tropsch products (hydrocarbons and water) and entrained synthesis gas. The withdrawn catalyst slurry in the flow line 50 is divided into a first portion 52 which is discarded and a second portion 54 which is sent to a catalyst reactivation facility 56. Typically the discarded catalyst 52 is subjected to a number of process steps to remove entrained synthesis gas and to separate the Fischer-Tropsch catalyst particles from Fischer-Tropsch product (not shown).

The details of the operation of the catalyst reactivation facility 56 are well known to those skilled in the art, e.g. as set out in U.S. Pat. No. 6,838,487 and US Patent Application No. 2002/0183403, and thus the catalyst reactivation facility 56 and the catalyst reactivation processes employed by the catalyst reactivation facility 56 are not described in any detail.

In one embodiment of the invention, the portion of withdrawn Fischer-Tropsch catalyst 54 that is fed to the catalyst reactivation facility 56 is subjected to a regeneration treatment by contacting the catalyst with a diluted air stream 62. Thereafter the regenerated (and oxidised) catalyst is subjected to a reduction step by the introduction of a hydrogen-containing stream 64 into the catalyst reactivation facility 56. The reactivated catalyst is then returned via flow lines 57 and 58 to the moving-bed Fischer-Tropsch synthesis reactor 16.

In an alternative embodiment, the portion of withdrawn Fischer-Tropsch catalyst 54 that is fed to the catalyst reactivation facility 56 is instead subjected to a rejuvenation treatment by contacting the catalyst with the hydrogen-containing stream 64 only, prior to the reactivated catalyst being returned via the flow lines 57 and 58 to the moving-bed Fischer-Tropsch synthesis reactor 16. That is, in the alternative embodiment, there is no regeneration treatment and thus no use of the diluted air stream 62.

In accordance with the method of the invention, fresh Fischer-Tropsch catalyst 60, in this embodiment corresponding in mass to the mass of discarded Fischer-Tropsch catalyst in the catalyst slurry portion 52, is added to the reactivated catalyst 58 and the combined stream introduced into the moving-bed Fischer-Tropsch synthesis reactor 16.

The catalyst reactivation facility 56 is operated on a batch basis, i.e. batches of Fischer-Tropsch catalyst (in the form of a slurry) are periodically withdrawn from the moving-bed Fischer-Tropsch synthesis reactor 16, a portion 54 is reactivated either by a regeneration treatment or a rejuvenation treatment and returned to the moving-bed Fischer-Tropsch synthesis reactor 16, and a portion 52 is discarded. However, the moving-bed Fisher-Tropsch synthesis reactor 16 is operated uninterruptedly, irrespective of whether catalyst containing slurry is withdrawn on a continuous or batch basis for reactivation purposes.

Prior Art Example

Figure 2:
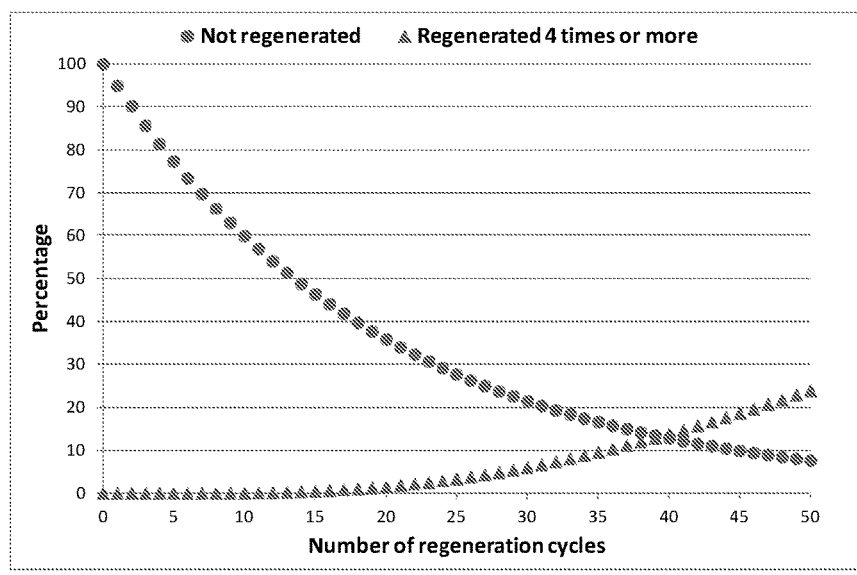
FIG. 2 shows a graph of the percentage of catalyst reactivated as a function of the number of reactivation cycles.

For the purposes of illustration, a closed-loop case, such as would be found in the methods of the prior art, is considered. In this case it is assumed that a Fischer-Tropsch catalyst can be withdrawn from a Fischer-Tropsch synthesis reactor and reactivated safely a maximum of four times and that a Fischer-Tropsch slurry reactor starts to experience significant operating problems when more than about 2.5 wt % of its Fischer-Tropsch catalyst inventory has reached or exceeded this limiting number of reactivation cycles. If 5 wt % of the catalyst inventory of the Fischer-Tropsch synthesis reactor is removed and reactivated per cycle, then the fraction of Fischer-Tropsch catalyst inside the Fischer-Tropsch synthesis reactor that has not been subjected to any reactivation cycles decreases after each reactivation cycle as indicated in FIG. 2. However, the fraction of catalyst inside the Fischer-Tropsch synthesis reactor that has been subjected to four or more reactivation cycles increases with every reactivation cycle, exceeding the limiting value of 2.5 wt % after 23 reactivation cycles. At this point, more than 30 wt % of the Fischer-Tropsch catalyst inventory of the Fischer-Tropsch synthesis reactor has never been reactivated. Since there is no convenient method to separate useful catalyst from spent catalyst, the whole catalyst inventory has to be discarded and the reactor is restarted with fresh catalyst. This requires interruption of the operation of the Fischer-Tropsch synthesis reactor, and is undesirable.

Example According to a Preferred Embodiment of the Invention

In a second case, operation of a moving-bed Fisher-Tropsch synthesis reactor employing a preferred embodiment of the method of the present invention is considered, i.e. where a portion of the withdrawn Fischer-Tropsch catalyst is discarded and a portion is reactivated and returned to the Fischer-Tropsch synthesis reactor. Discarding of a portion of the withdrawn Fischer-Tropsch catalyst according to the method of the invention is necessary in order to prevent the problem of spent catalyst, and in particular spent catalyst subjected to four or more reactivation cycles, building up in the Fisher-Tropsch reactor, as exemplified in Example 1.

Figure 3:
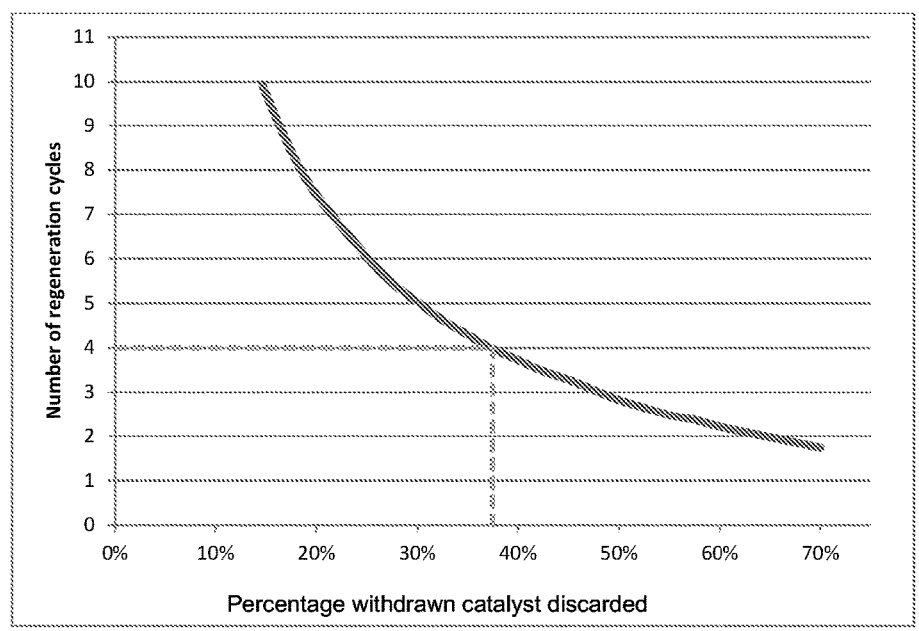
FIG. 3 shows a graph of the percentage of withdrawn Fischer-Tropsch catalyst that has to be discarded (and made up with fresh Fischer-Tropsch catalyst) as a function of the number of reactivation cycles that a catalyst can tolerate.

FIG. 3 shows the percentage of withdrawn Fischer-Tropsch catalyst that has to be discarded (and made up with fresh Fischer-Tropsch catalyst) as a function of the numbers of reactivation cycles that a catalyst can tolerate. In Example 1, the catalyst was assumed to be able to tolerate up to a maximum of four reactivation cycles. At four reactivation cycles, approximately 37.5 wt % of each batch of the withdrawn Fischer-Tropsch catalyst is required to be discarded, with only the remaining portion of each batch (62.5 wt %) being subjected to the reactivation process before being returned to the Fischer Tropsch synthesis reactor.

The method of the present invention, as illustrated, holds a number of advantages over the methods described in the art. Firstly, the Fischer-Tropsch reactor can be run for an indefinite period without ever exceeding a limiting amount of spent catalyst inside the Fischer-Tropsch reactor, as would be the case for the closed-loop method of Example 1. This mitigates the need for shutting down or interrupting Fisher-Tropsch synthesis periodically due to a build-up of spent catalyst, enabling much longer production campaigns. Secondly, the average activity of the Fischer-Tropsch catalyst inventory inside the Fischer-Tropsch reactor remains substantially constant, meaning that the Fischer-Tropsch process can be run at or very close to its optimum operating conditions for substantially a full production campaign.

Notwithstanding that the method of the present invention requires the discarding of potentially significant amounts of Fischer-Tropsch catalyst that is fit for continued use in the Fischer-Tropsch synthesis process as is shown in FIG. 3, it has surprisingly been found that the method of the present invention has a net economic benefit over other known approaches due to the foregoing advantages, at least in some cases.

The invention claimed is:

1. A method of synthesising Fischer-Tropsch products, the method including
    feeding a synthesis gas to a moving-bed Fischer-Tropsch synthesis reactor containing a Fischer-Tropsch catalyst in a moving catalyst bed, catalytically converting at least a portion of the synthesis gas in the moving catalyst bed to Fischer-Tropsch products and withdrawing the Fischer-Tropsch products from the moving-bed Fischer-Tropsch synthesis reactor,
    the method further including, while the moving-bed Fischer-Tropsch synthesis reactor is on-line:
        withdrawing a portion of the Fischer-Tropsch catalyst from the moving-bed Fischer-Tropsch synthesis reactor;
        discarding from about 15 wt % to about 60 wt % of the withdrawn Fischer-Tropsch catalyst;
        adding a reactivated Fischer-Tropsch catalyst to the moving-bed Fischer-Tropsch synthesis reactor; and
        adding a fresh Fischer-Tropsch catalyst, in addition to the reactivated catalyst, to the moving-bed Fischer-Tropsch synthesis reactor.

2. The method according to claim 1, wherein at least a portion of the withdrawn Fischer-Tropsch catalyst is subjected to a reactivation treatment thereby to produce at least a portion of the reactivated Fischer-Tropsch catalyst.

3. The method according to claim 2, wherein the reactivation treatment includes a regeneration treatment and wherein the regeneration treatment includes exposing the withdrawn catalyst to oxygen.

4. The method according to claim 3, wherein the regeneration treatment includes a reduction step which includes exposing the withdrawn Fisher-Tropsch catalyst to hydrogen, subsequent to exposing the withdrawn Fischer-Tropsch catalyst to oxygen.

5. The method according to claim 2, wherein the reactivation treatment includes a rejuvenation treatment and wherein the rejuvenation treatment includes exposing the withdrawn Fischer-Tropsch catalyst to hydrogen.

6. The method according to claim 1, wherein the on-line withdrawal of the portion of the Fischer-Tropsch catalyst from the moving-bed Fischer-Tropsch synthesis reactor is done batch-wise.

7. The method according to claim 6, wherein the portion of the Fischer-Tropsch catalyst withdrawn from the moving-bed Fisher-Tropsch synthesis reactor per batch is in the range of from about 0.1 wt % to about 10 wt % of a Fischer-Tropsch catalyst inventory in the moving-bed Fisher-Tropsch synthesis reactor.

8. The method according to claim 1, wherein the fresh Fischer-Tropsch catalyst is added to the moving-bed Fischer-Tropsch synthesis reactor in a mass which is selected to match the mass of the discarded portion of withdrawn Fischer-Tropsch catalyst.

9. The method according to claim 1, wherein the moving-bed Fischer-Tropsch synthesis reactor is a slurry phase reactor which employs a supported cobalt catalyst and wherein an operating temperature of the moving-bed Fischer-Tropsch synthesis reactor is in the range of from about 200° C. to about 240° C.

* * * * *